US012565372B2

(12) United States Patent
Leibbrand et al.

(10) Patent No.: US 12,565,372 B2
(45) Date of Patent: Mar. 3, 2026

(54) PACKAGING FOR A PLURALITY OF UNIT MEDICAL VESSELS AND PROCESSING SYSTEM IMPLEMENTING SUCH PACKAGING

(71) Applicant: Becton Dickinson France, Le Pont-de-Claix (FR)

(72) Inventors: Alfred Leibbrand, Claix (FR); Pauline Poncet, Revel (FR); Pauline Honore, Paris (FR); Jordan Giner, Mauguio (FR); Anthony Lavoine, Bures-sur-Yvette (FR)

(73) Assignee: Becton Dickinson France, Le Pont-de-Claix (FR)

( * ) Notice: Subject to any disclaimer, the term of this patent is extended or adjusted under 35 U.S.C. 154(b) by 113 days.

(21) Appl. No.: 18/585,986

(22) Filed: Feb. 23, 2024

(65) Prior Publication Data

US 2024/0239592 A1     Jul. 18, 2024

(51) Int. Cl.
| | |
|---|---|
| *B65D 83/02* | (2006.01) |
| *A61M 5/00* | (2006.01) |
| *B65B 3/00* | (2006.01) |
| *B65B 55/02* | (2006.01) |
| *B65D 73/02* | (2006.01) |
| *B65D 77/06* | (2006.01) |
| *B65D 81/22* | (2006.01) |

(52) U.S. Cl.
CPC ............. *B65D 83/02* (2013.01); *A61M 5/002* (2013.01); *B65B 3/003* (2013.01); *B65B 55/027* (2013.01); *B65D 73/02* (2013.01);

*B65D 77/06* (2013.01); *B65D 81/22* (2013.01); *B65D 2577/042* (2013.01)

(58) Field of Classification Search
CPC ........ B65D 83/02; B65D 73/02; B65D 77/06; B65D 81/22; B65D 2577/042; A61M 5/002; B65B 3/003; B65B 55/027
USPC ........... 221/25; 206/365, 820, 366, 441, 438
See application file for complete search history.

(56) References Cited

U.S. PATENT DOCUMENTS

| | | | | |
|---|---|---|---|---|
| 1,386,398 A | * | 8/1921 | Davis ....................... | A47K 1/09 |
| | | | | 206/820 |
| 5,245,117 A | * | 9/1993 | Withers ................ | A61M 5/002 |
| | | | | 405/129.55 |
| 6,164,044 A | | 12/2000 | Porfano et al. | |

(Continued)

FOREIGN PATENT DOCUMENTS

| | | |
|---|---|---|
| EP | 0439740 A1 | 8/1991 |
| EP | 0935969 B1 | 8/2005 |

(Continued)

*Primary Examiner* — Chun Hoi Cheung
(74) *Attorney, Agent, or Firm* — The Webb Law Firm

(57) ABSTRACT

A packaging for a plurality of unit medical vessels, including at least one foldable strip of unit medical vessels and a primary container defining a hermetically sealed inner volume inside the peripheral wall. The foldable strip of unit medical vessels is received in said inner volume of the primary container. The primary container has a transfer port having a closure. The closure having a closed configuration where, in the closed state of the primary container, it hermetically closes the transfer port, and an open configuration where it allows the at least one foldable strip of unit medical vessels to be transferred out of the primary container through the transfer port.

20 Claims, 8 Drawing Sheets

(56)  References Cited

U.S. PATENT DOCUMENTS

| | | | | |
|---|---|---|---|---|
| 7,556,149 B2 * | 7/2009 | Erickson | ............... | A61M 5/002 |
| | | | | 206/365 |
| 7,815,046 B2 * | 10/2010 | Sansoucy | ........... | A61B 50/3001 |
| | | | | 221/102 |
| 8,002,113 B1 * | 8/2011 | Cummings | .......... | B65D 85/672 |
| | | | | 206/820 |
| 8,074,834 B2 * | 12/2011 | O'Hara | ................ | A61F 13/041 |
| | | | | 229/125.21 |
| 8,113,349 B2 * | 2/2012 | Sansoucy | .............. | A61M 5/002 |
| | | | | 206/370 |
| 8,944,245 B2 * | 2/2015 | Erickson | ............. | A61M 5/3205 |
| | | | | 206/438 |
| 11,147,911 B2 * | 10/2021 | Wendland | ........... | A61M 5/2033 |
| 2003/0132129 A1 * | 7/2003 | Erickson | ............. | A61M 5/3205 |
| | | | | 206/366 |
| 2004/0261358 A1 | 12/2004 | Liedtke | | |
| 2011/0011881 A1 * | 1/2011 | Sansoucy | .............. | A61M 5/002 |
| | | | | 221/102 |
| 2013/0233876 A1 * | 9/2013 | Teates | ................... | A61F 15/002 |
| | | | | 221/70 |

FOREIGN PATENT DOCUMENTS

| | | | |
|---|---|---|---|
| EP | 2453947 | B1 | 6/2018 |
| WO | 2008085969 | A2 | 7/2008 |

\* cited by examiner

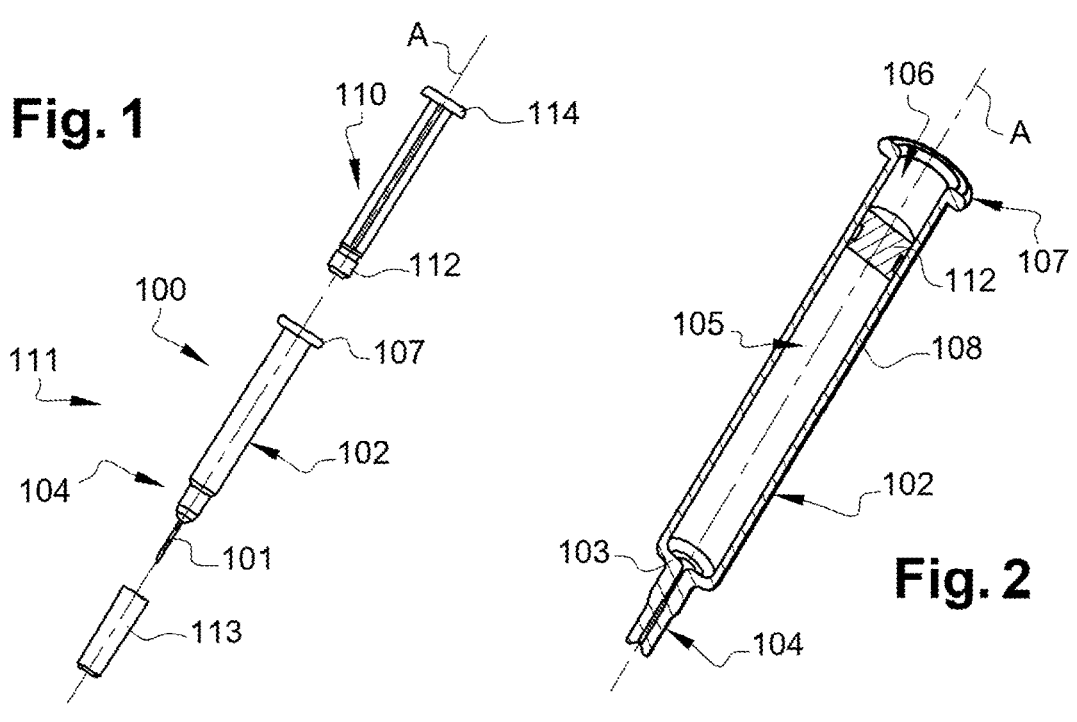
Fig. 1
Fig. 2
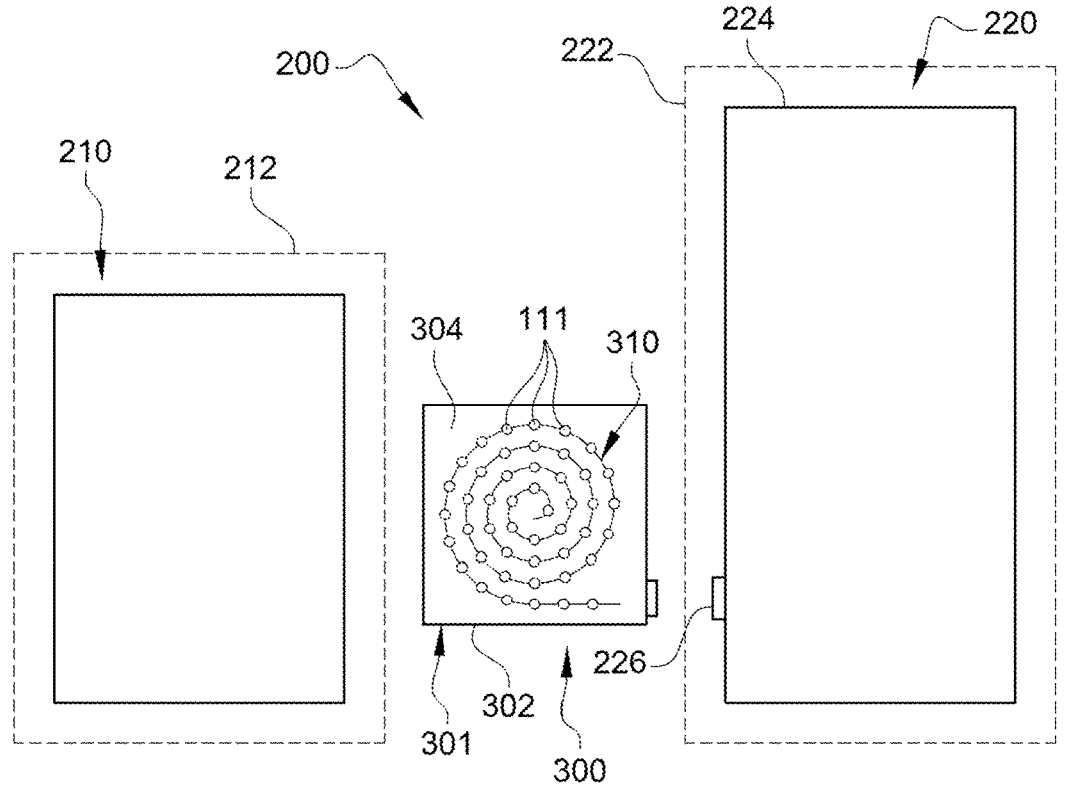
Fig. 3

PACKAGING FOR A PLURALITY OF UNIT MEDICAL VESSELS AND PROCESSING SYSTEM IMPLEMENTING SUCH PACKAGING

BACKGROUND OF THE INVENTION

Field of the Invention

The invention relates to the field of packaging for unit medical vessels. The invention may be applied to unit medical vessels being syringes, such as prefilled or pre-fillable syringes, especially syringes for delivering a drug to a patient.

Description of Related Art

Unit medical vessels are designed to contain a medical product, typically a powder or liquid medical product such as a liquid drug. Unit medical vessels may be in the form bottles, vials, syringes, etc. . . . Unit medical vessels may be made of plastic or glass. From the moment the unit medical vessel is manufactured till the moment the unit medical vessel, filled with a medical product, is used by an end user, many processing steps need to be carried out. A key processing step is the step of filling the unit medical vessel with the medical product. Other processing steps may include cleaning, sterilizing, closing, labelling, inspecting, assembling and/or shipping the unit medical vessel, et cetera. In modern industrial high-volume production of unit medical vessels filled with a medical product, it is very unlikely that all of these processing steps are performed at the same location and or on the same machine. There is thus a need to transport the unit medical vessels from one place to another, from one machine to another, possibly at different points in time. During such transport, even if over a short distance, the unit medical vessels need to be handled and stored, in large numbers, and need to be protected at least to some extent against mechanical shocks and/or against contamination. During such transport, the unit medical vessel may be empty or may be filled with the medical product.

During such transport, a plurality of unit medical vessels are conventionally stored into a secondary packaging, this secondary packaging comprising a nest supporting the medical containers, a housing or tub containing the nest, a sealing cover closing the tub, and a so-called header bag ensuring some level of protection against contamination. Alternatively, documents WO2008085969A2, EP0439740, and EP2453947A1 disclose different prior art forms of packaging for unit medical vessels. Such forms of packaging usually comprises a nest in the form of a tray defining an array of locations at each of which an individual unit medical vessel is located. Such known forms packaging are very satisfactory for safely transporting unit medical vessels and preventing contamination and/or damage of the vessels. However, the step of packing the unit medical vessels into such packaging, and of unpacking the unit medical vessels from such packaging, for performing another processing step in the global production and transport process, may need special care, especially when, before the packing or after the unpacking, the unit medical vessels are to be processed by some machinery where the unit medical vessels are processed in line.

The invention therefore aims at providing packaging for unit medical vessels that may improve the processability, including easiness of packing and/or unpacking the unit medical vessels into or out of such packaging, while still maintaining low cost and adequate protection of the unit medical vessels from mechanical damage and from external contamination.

SUMMARY OF THE INVENTION

The disclosure provides for a packaging for a plurality of unit medical vessels, comprising:

at least one foldable strip of unit medical vessels in which a plurality of unit medical vessels are connected one to the other at spaced intervals along a strip elongation path, wherein the foldable strip is foldable at least around a plurality of principal folding axis spaced apart along the strip elongation path, each principal folding axis being perpendicular to the strip elongation path; and a primary container having a peripheral wall and having a closed state in which the primary container defines a hermetically sealed inner volume inside the peripheral wall, wherein the foldable strip of unit medical vessels is received in said inner volume of the primary container, and wherein the primary container has a transfer port having a closure, the closure having a closed configuration where, in the closed state of the outer bag, it hermetically closes the transfer port, and an open configuration where it allows the at least one foldable strip of unit medical vessels to be transferred out of the primary container through the transfer port.

In some embodiments, the primary container contains a single foldable strip of unit medical vessels.

In some embodiments, in the closed state of the primary container, the inner volume of the primary container is filled with a sterilizing fluid.

In some embodiments, in the closed state of the primary container, the inner volume of the primary container is filled with a fluid under a pressure superior to the atmospheric pressure.

In some embodiments, the peripheral wall of the primary container has at least one flexible wall portion.

In some embodiments, the peripheral wall of the primary container is flexible.

In some embodiments, the peripheral wall of the primary container has at least one rigid wall portion.

In some embodiments, the peripheral wall of the primary container is rigid.

In some embodiments, the primary container has a main opening which is distinct from the transfer port, through which the at least one foldable strip of unit medical vessels is introduced in the inner volume of the primary container, and which is hermetically sealed when the primary container is in its closed state.

In some embodiments, the primary container has a sterilizing fluid introduction port, which is distinct from the transfer port.

In some embodiments, the unit medical vessels of the plurality of unit medical vessels are arranged in a single row along the strip elongation path of the foldable strip of unit medical vessels.

In some embodiments, the unit medical vessels of the plurality of unit medical vessels are each elongated along a vessel axis parallel to the principal folding axis direction.

In some embodiments, the foldable strip of unit medical vessels comprises a foldable carrier strip on which the unit medical vessels of the plurality of unit medical vessels are affixed along the strip elongation path, wherein the foldable carrier strip is foldable at least around said plurality of principal folding axis spaced apart along the strip elongation path.

In some embodiments, the unit medical vessels are each individually removably affixed on the foldable carrier strip.

In some embodiments, the foldable carrier strip comprises a flexible tie which extends along the strip elongation path and on which the unit medical vessels or the plurality of unit medical vessels are affixed along the strip elongation path, wherein the flexible tie is foldable at least around said plurality of principal folding axis spaced apart along the strip elongation path.

In some embodiments, the foldable carrier strip comprises several successive rigid segments which each extend along a portion of the strip elongation path and on which the unit medical vessels of the plurality of unit medical vessels are affixed at equally spaced intervals along the strip elongation path, and wherein two successive rigid segments along the strip elongation path, are articulated one to the other around one of said principal folding axis.

In some embodiments, the foldable strip of unit medical vessels comprises a series of connectors where each connector extends between two unit medical vessels, and each of said two unit medical vessels is removably affixed to the connector.

In some embodiments, two successive connectors, having a common unit medical vessel affixed respectively to the two successive connectors, are independent from one another and said unit medical vessel is independently and removably affixed to each of to the two successive connectors.

In some embodiments, the connector is flexible.

In some embodiments, each of said two unit medical vessels is removably and rotatably affixed to the connector.

The disclosure also provides for a processing system for processing unit medical vessels, wherein the processing system comprises a processing station having a closed enclosure which is sealed from an external environment outside of the enclosure, wherein the unit medical vessels are processed inside the closed enclosure, wherein the enclosure of the processing station has an input docking port, wherein the input docking port is compatible with the transfer port of a primary container of a packaging according any of the preceding claims to achieve a sealed docking of the primary container on the processing station, and wherein, when the primary container is sealingly docked on the processing station, the closure of the transfer port may be set to its open configuration where the transfer port allows communication between the inner volume of the primary container and the inside of the closed enclosure of the processing station, and where the transfer port allows the foldable strip of unit medical vessels to be transferred out of the primary container through the transfer port and the input docking port into the inside of the closed enclosure of the processing station, without contact with the external environment.

In some embodiments, the processing system is a filling system for filing the unit medical vessels with a medical product, wherein the processing station is a filling station having a closed enclosure which is sealed from an external environment outside of the closed enclosure and in which the unit medical vessels are filled with a medical product inside the closed enclosure.

BRIEF DESCRIPTION OF THE DRAWINGS

The terms Fig., Figs., Figure, and Figures are used interchangeably in the specification to refer to the corresponding figures in the drawings.

FIG. 1: FIG. 1 is a schematic perspective and exploded view of a syringe as an example of a unit medical vessel.

FIG. 2: FIG. 2 is a schematic longitudinal cutaway perspective view of the syringe barrel as an example of a unit medical vessel.

FIG. 3: FIG. 3 is a diagram of a portion of processing system for processing unit medical vessels.

FIG. 4 is the schematic side view of a first example of a foldable strip of unit medical vessels.

FIG. 5 is a schematic top view of the first example of a foldable strip of unit medical vessels.

FIG. 6 is a schematic top view of a first variant of a foldable carrier strip for a foldable strip of unit medical vessels.

Figures 7, 8, 9:
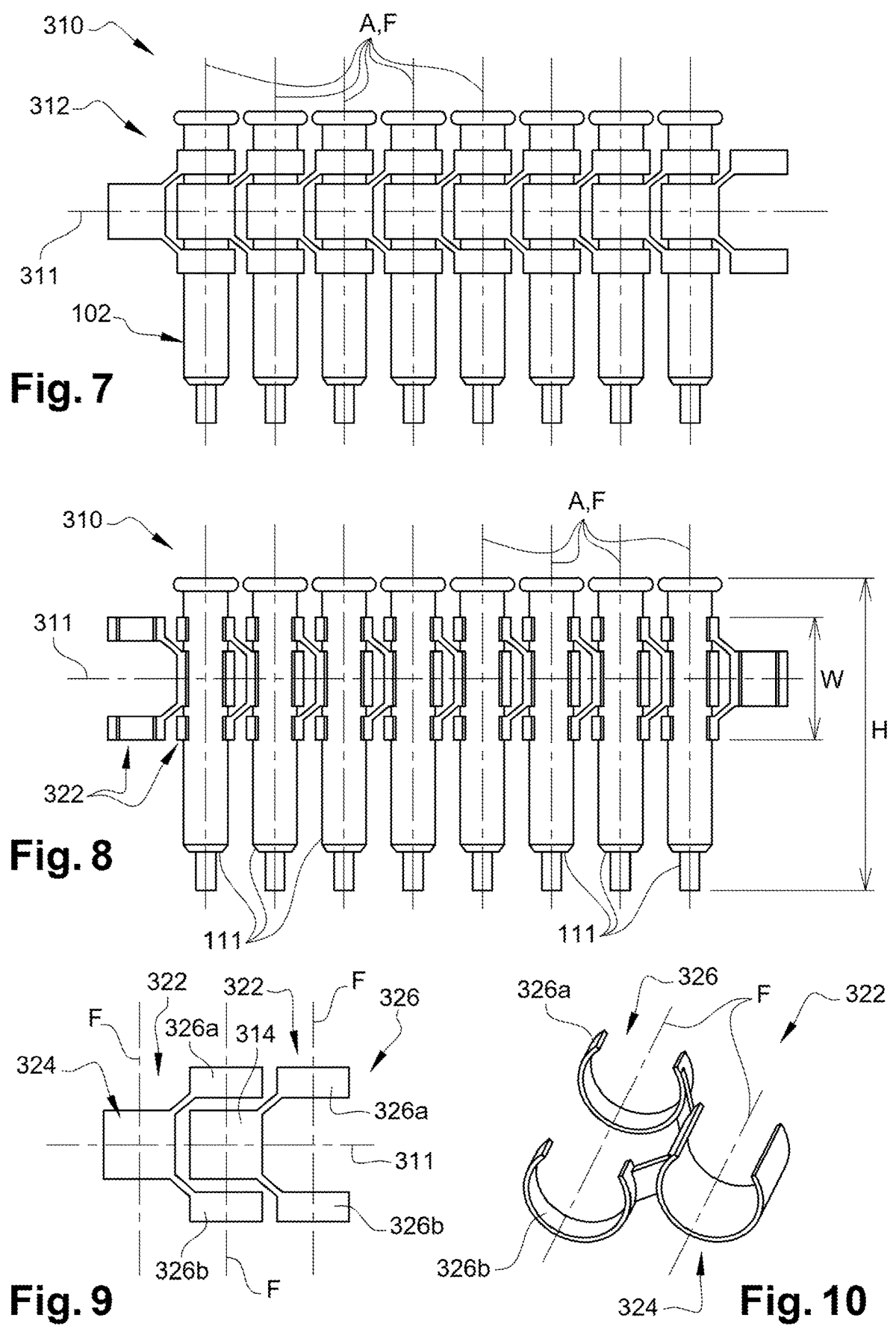

FIG. 7: FIG. 7 is a schematic first side view of a second variant of a foldable strip of unit medical vessels.

FIG. 8: FIG. 8 is a schematic second side view of the second variant of FIG. 7.

FIG. 9: FIG. 9 is a side view of a pair of connectors of the second variant of FIG. 7.

FIG. 10: FIG. 10 is a perspective view of a connector of the second variant of FIG. 7.

FIG. 11 is a schematic first side view of a third variant of a foldable strip of unit medical vessels.

FIG. 12 is a schematic second side view of the third variant of FIG. 11.

FIG. 13 is a schematic perspective view of a first example of a packaging for a plurality of unit medical vessels, shown in the closed state, with the closure in a closed configuration.

FIG. 14 is a perspective view of the first example of the packaging, shown in an open state, with the closure in an open configuration.

FIG. 15 is a schematic perspective view of a fourth variant of a foldable strip of unit medical vessels and of a variant of a primary container forming a second example of a packaging for a plurality of unit medical vessels.

FIG. 16 is a schematic perspective view of the second example of the packaging of FIG. 15, with a partial cutout, with its closure in the open configuration.

FIG. 17 is an example of a palletized pack of packaging for a plurality of unit medical vessels according to the second example of FIG. 15.

FIG. 18 is a schematic top view of a primary container and of a filling station, before the docking of the primary container on the filling station.

FIG. 19 is a view similar to that of FIG. 18, where the primary container is docked on the filling station, the closure of the primary container being still in a closed configuration.

FIG. 20 is a view similar to that of FIGS. 18 and 19, where the primary container is docked on the filling station, the closure of the primary container being in the open configuration.

DESCRIPTION OF THE INVENTION

Figure 4:
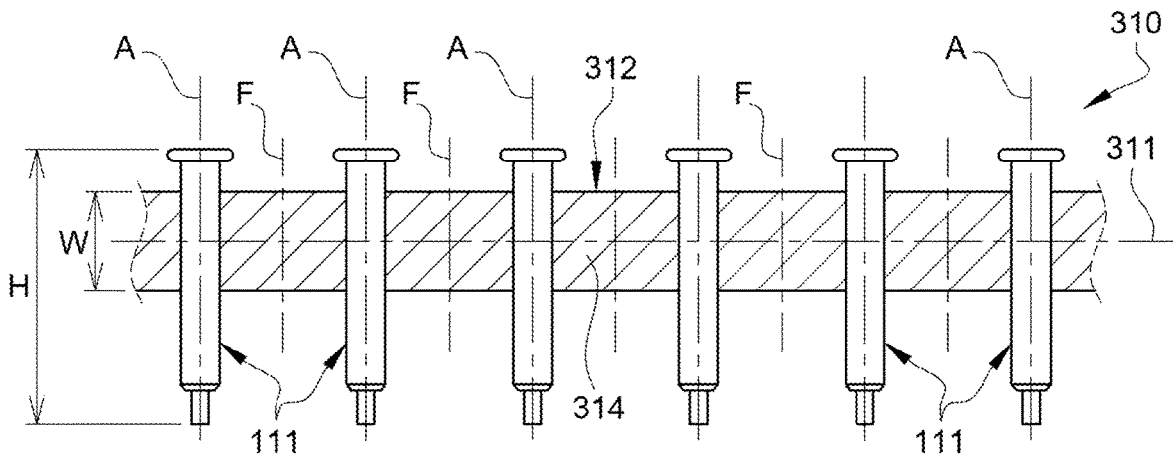
FIG. 4.

FIG. 1 shows an example of a unit medical vessel 111, in the form of a typical syringe assembly. In this application, where a syringe 100 is designed to be handled by a user, typically a health professional during use, for instance during injection, the distal end of a component or of a device is to be understood as meaning the end furthest from the user's hand and the proximal end is to be understood as meaning the end closest to the user's hand. Likewise, in this application, the "distal direction" is to be understood as meaning the direction of injection along a longitudinal axis, and the "proximal direction" is to be understood as meaning the opposite direction to said direction of injection along the longitudinal axis, that is to say the direction towards the user's hand.

The syringe 100 may be a prefilled or prefillable syringe. The syringe 100 includes a barrel 102, of tubular shape, having, along a longitudinal axis A, a proximal end, a distal end, and a tip 104 at its distal end. As more clearly visible in FIG. 2, the barrel 102 defines an internal reservoir 105 which is designed for containing a medical product such as a drug which may be for example under liquid form. The barrel 102 may be made of a plastic or of a glass material. This barrel 102 has, at its distal end, a distal shoulder 103 provided with the distal tip 104 longitudinally protruding in the distal direction from said distal shoulder 103 along the longitudinal axis A. The distal tip 104 defines a longitudinal passageway in fluid communication with the reservoir and is designed to be equipped with an injection needle 101 for injecting the medical product in an injection site. The injection needle 101 can be connected to the distal tip 104, for example via a Luer-type connection, e.g. a Luer-cone or Luer-lock connection in which the user attaches the needle at the time of injection, or via a staked or pre-attached needle in which the injection cannula is already pre-attached, for example via an adhesive. The barrel 102 further includes an open proximal end 106 which comprises a radial flange 107. The open proximal end 106 receives a plunger rod 110 for pushing a stopper 112 which is received inside the barrel 102. The stopper 112 is able to slide longitudinally in a fluid-tight manner inside the internal reservoir 105 under the action of the plunger rod 110 to which it is connected. When the stopper 112 is pushed along the distal direction by the plunger rod 110, it causes the expulsion of the medical product from the reservoir to the injection site via the longitudinal passageway through the distal tip 104 and the injection needle 101. The plunger rod 110 typically comprises, at its proximal end, a plunger flange 114 whose proximal facing surface forms a contact surface for the thumb of a user.

The syringe therefore comprises the barrel 102, with its distal tip 104. A syringe assembly 111 may comprise, in addition to the barrel 102, one or more of the injection needle 101, the stopper 112, the plunger rod 110, a tip cap 113 for protecting and sealing the injection needle 101 before injection, an intermediate cap closing the distal tip 104 of the barrel 102 before mounting of an injection needle on the distal tip 104, et cetera.

In the following example, a unit medical vessel can be formed either by the syringe barrel in itself, or by any form of a syringe assembly.

FIG. 3 is a diagrammatic view of a processing system 200 for processing unit medical vessels. The processing system comprises a first processing station 210 and a second processing station 220. The unit medical vessels 111 need to be transported from the first processing station 210 to the second processing station 220. The first processing station 210 may be in a first processing entity 212 and the second processing station 220 may be in a second processing entity 222. The second processing station 220 comprises a closed enclosure 224 which is sealed from an external environment outside of the closed enclosure 224. In the shown example FIG. 3, the external environment outside of the closed enclosure 224 is the environment of the second processing entity 222. The second processing entity 222 may be a cleanroom, an isolator or a Restricted Access Barrier System (RABS) within the building, or may be the building itself or may be an outside environment. It is to be noted that the first processing station and the second processing station 220 may be in a same cleanroom or a same Restricted Access Barrier System (RABS), and/or in the same building, or not. The unit medical vessels 111 are processed inside the closed enclosure 224.

As an example, the processing system 200 may be a system for fabricating the unit medical vessels 111 and for filing the unit medical vessels 111 with a medical product. In such a system, the first processing station 210 may thus be a fabricating station where the unit medical vessels 111 are manufactured and packed in a packaging. The first processing entity 212 where the fabricating station 210 is located may be a manufacturing plant 212, or a cleanroom or a Restricted Access Barrier System (RABS) in a manufacturing plant. The second processing station 220 is for example a filling station having the closed enclosure 224 which is sealed from an external environment outside of the closed enclosure and in which the unit medical vessels hundred 11 are filled with a medical product. The second processing entity 222 may be a cleanroom or a Restricted Access Barrier System (RABS) located in a filling plant, which may be distant from the manufacturing plant 212.

In the example, the closed enclosure 224 of the filling station 220 has an input docking port 226 through which the unit medical vessels 111 are to be entered into the closed enclosure 224 of the filling station 220.

In general terms, the unit medical vessels 111 are thus to be transported from the first processing station 210, which is here a fabricating station, to the second processing station, which is here the filling station 220, while being protected, at least to a certain extent, from external mechanical shocks and from fouling. Therefore, the unit medical vessels 111 are packed into a packaging 300 for their transport between the first processing station 210 to the second processing station 220. In the example, the step of packing the unit medical vessels 111 into packaging 300 may be performed in the fabricating station 210. At the second processing station, the unit medical vessels 111 need to be unpacked from the packaging 300.

Figure 13:
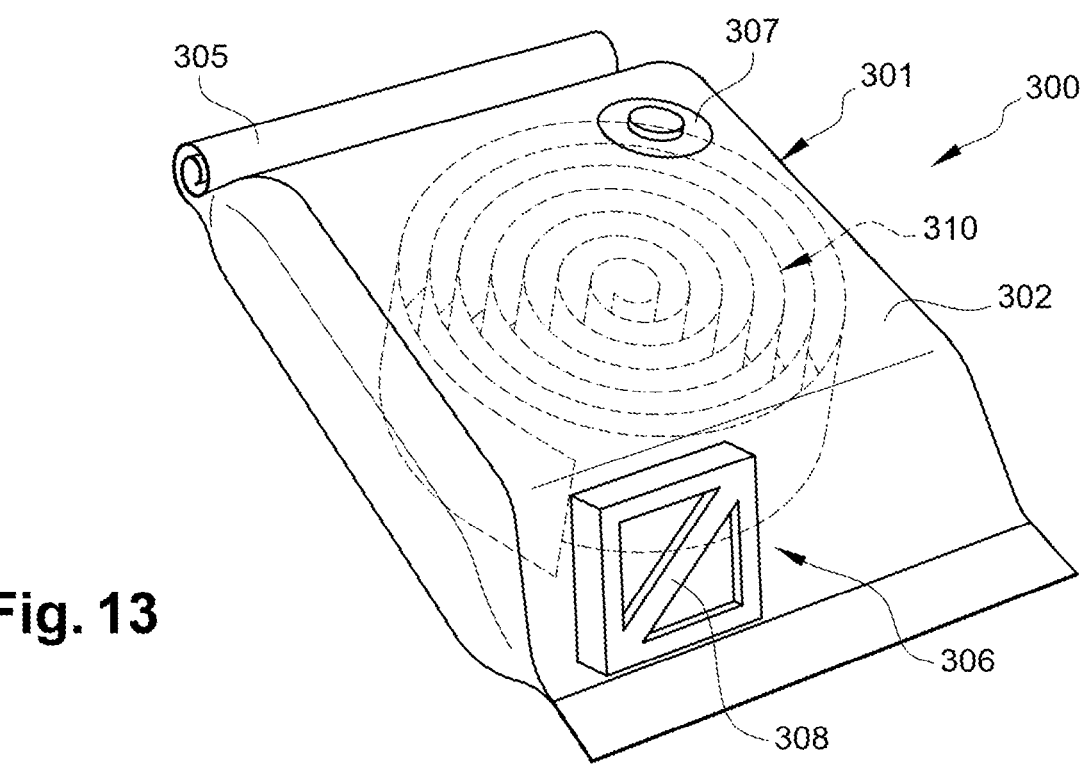
FIG. 13.

As already illustrated schematically in FIG. 3, the packaging 300 comprises a primary container 301 having a peripheral wall 302 and having a closed state, shown for example in FIG. 13 in one particular example, in which the primary container 301 defines a hermetically sealed inner volume 304 inside the peripheral wall 302. The peripheral wall 302 completely surrounds the inner volume 304 in all directions.

The packaging 300 also comprises a foldable strip 310 of unit medical vessels 111 in which a plurality of unit medical vessels 111 are connected one to the other at equally spaced intervals along a strip elongation path 311. The foldable strip 310 of unit medical vessels 111 is received in said inner volume 304 of the primary container 301 in its closed state.

Figure 14:
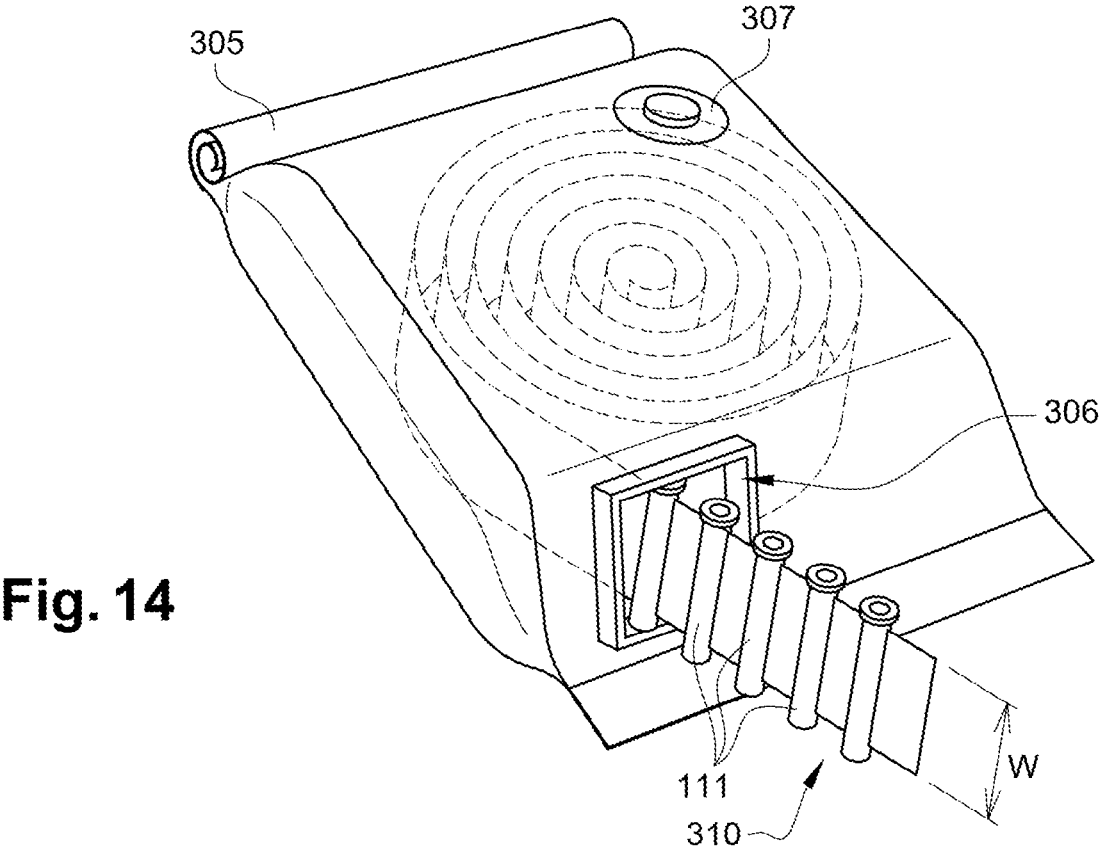
FIG. 14.

The primary container 301 has a transfer port 306 having a closure 308, the closure having a closed configuration, shown for example in FIG. 13 in one particular example, where, in the closed state of the primary container 301, the closure 308 hermetically closes the transfer port 306, and an open configuration, shown for example in FIG. 14 for the same example, where it allows the foldable strip 310 of unit medical vessels 111 to be transferred out of the primary container for 300 through the transfer port 306.

Figure 5:
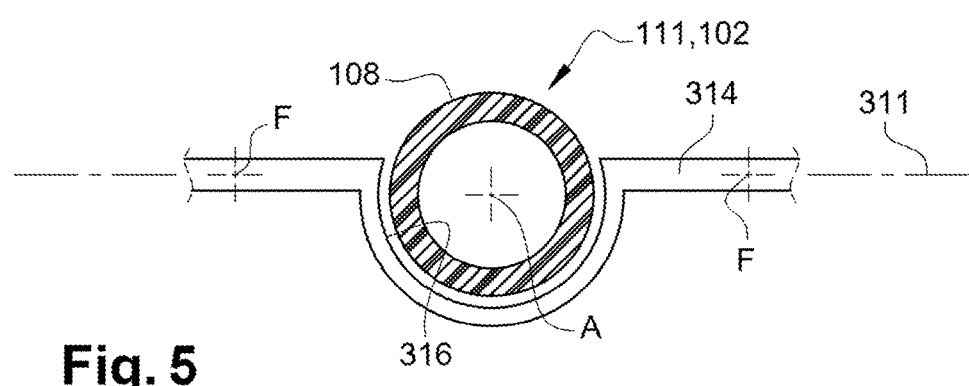
FIG. 5.

An example embodiment of a foldable strip 310 is shown on FIGS. 4 and 5, and is further described in document EP-0.935.969-A2 which is herein incorporated by reference. A first variant of such a foldable strip is shown on FIG. 6, and is also further described in document EP-0.935.969-A2 which is herein incorporated by reference. A second variant of such a foldable strip is shown on FIGS. 7 to 10. A third variant of such a foldable strip is shown on FIGS. 11 and 12. A fourth variant of such a foldable strip is shown on FIGS. 15 and 16

A foldable strip 310 of unit medical vessels 111 is finite in length and thus contains a defined number of unit medical vessels 111, for example 20, 50, 100, 200 or 500 unit medical vessels 111.

In all illustrated variants, the foldable strip 310 is foldable at least around a plurality of principal folding axis F spaced apart along the strip elongation path 311, each principal folding axis F being parallel to a principal folding axis direction perpendicular to the strip elongation path 311.

In all illustrated variants, the unit medical vessels 111 of the plurality of unit medical vessels are arranged in a single row along the strip elongation path 311 of the foldable strip 310 of unit medical vessels 111. However, it would be possible to have them arranged in several rows, for example two rows side-by-side, or back-to-back. In such a case, two corresponding unit medical vessels 111 of each row may be at a corresponding location along the strip elongation pass 311, or may be offset along the strip elongation path 311, for example by half of the pitch between two successive unit medical vessels 111 of a given row.

Figure 6:
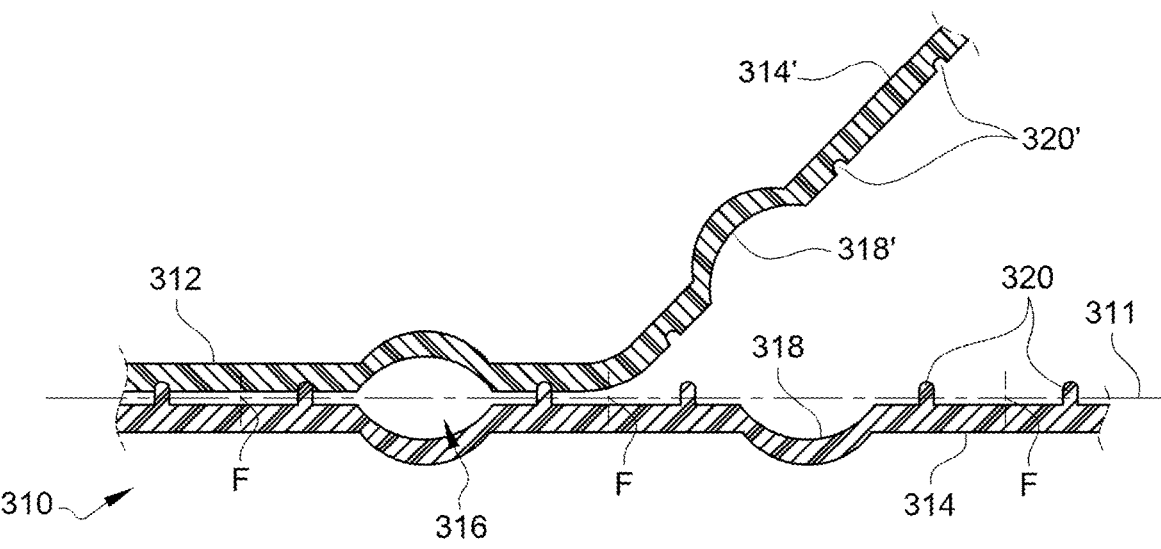
FIG. 6.

In the example embodiment of FIGS. 4 and 5 and in the first variant of FIG. 6, the foldable strip 310 of unit medical vessels 111 comprises a foldable carrier strip 312 on which the unit medical vessels 111 of the plurality of unit medical vessels are affixed at spaced intervals along the strip elongation path 311, those intervals being preferably equally spaced.

Each unit medical vessels 111 is individually removably affixed on the foldable carrier strip 312, for example by a snap-fit connection and/or through a removable adhesive connection that preferably leaves no adhesive on the vessel after removal. Thereby, each unit medical vessel can be removed from the foldable carrier strip 312 when needed, at the appropriate processing station, such that each unit medical vessel may be processed individually. Preferably, each unit medical vessel can be removed from the foldable carrier strip 312 by the mere application of opposite separation forces respectively on the unit medical vessel and on the foldable carrier strip 312. In other words, the separation of a unit medical vessel from the foldable carrier strip 312 preferably does not require any other action than holding the unit medical vessel 111 and the foldable carrier strip 312 and displacing them away one from the other. Preferably, each unit medical vessel can be removed from the foldable carrier strip 312 without any damage to unit medical vessel. Preferably, each unit medical vessel can be removed from the foldable carrier strip 312 without any damage to the foldable carrier strip 312, so that the foldable carrier strip 312 may be subsequently reused for forming a new foldable strip 310. However, in some embodiments, the removal of the unit medical vessels 111 from foldable carrier strip 312 may involve partial or complete destruction of the foldable carrier strip 312, which is then disposable, but preferably made of recyclable material.

In the example embodiment of FIGS. 4 and 5 and in the first variant of FIG. 6, the foldable carrier strip 312 comprise a flexible tie 314 that extends along the strip elongation path 311. In those examples and variants, the foldable carrier strip 312 is continuous and self-standing along the length of the foldable strip 310. In those examples and variants, the foldable strip 310 of unit medical vessels comprises the foldable carrier strip 312 and the unit medical vessels 111, which are affixed on the foldable carrier strip 312.

In the shown examples, each unit medical vessel 111 is an elongated vessel having a longitudinal vessel axis A. Preferably, in such a case, the longitudinal vessel axis A of each unit medical vessel 111 is arranged perpendicularly to the strip elongation path 311 when the unit medical vessel 111 is affixed in the foldable strip 310. Preferably, the unit medical vessels 111 are all arranged parallel one to the other in the foldable strip 310, with their longitudinal axis A being parallel one to the other, and being perpendicular to that strip elongation path 311. In such case, the principal folding axis direction of the foldable strip 310 is parallel to that longitudinal vessel axis A of the unit medical vessels 111 in the foldable strip 310. However, in a possible variant, the longitudinal vessel axis A of each unit medical vessel 111 may be arranged with an angle, for example comprised in the range from 65 to 115 degrees, with respect to the strip elongation path 311 when the unit medical vessel 111 is affixed in the foldable strip 310. Such a non-strictly perpendicular relative orientation may be advantageous for facilitating the removal of the unit medical vessels from the foldable strip, and/or may be useful for reducing the size of the transfer port 306 of the primary container 301.

In the example embodiment of FIGS. 4 and 5, the flexible tie 314 may be in the shape of a belt that is elongated along the strip elongation path. The belt 314 has a width W, perpendicularly to the strip elongation path 311, and has a thickness perpendicularly to the strip elongation path 311 and to the width. In the first, second and third variants shown respectively in FIGS. 4, 8 and 11, the width W of the belt 314, thus the width of the flexible carrier strip 312, is less than the height H of the unit medical vessels 111 along the same direction. In other words, the unit medical vessels 111 exceed the limits of the flexible carrier strip 312 along the width direction of the flexible carrier strip 312, at least on one side, or, as in the shown embodiment of FIGS. 4 and 5, on both sides along the width direction of the flexible strip 310. In an alternate design, the unit medical vessels 111 could be within the limits of the flexible carrier strip 312 along the width direction of the flexible carrier strip 312, at least on one side, thereby having at least one longitudinal extremity of the unit medical vessels 111 protected by the flexible carrier strip 312. In some examples, such as in the fourth variant shown in FIGS. 15 and 16, the width W of the flexible carrier strip 312 is such that each unit medical vessel 111 is contained within the limits of the flexible carrier strip 312 along the width direction of the flexible carrier strip 312. In such examples, both longitudinal extremities of each unit medical vessel 111 are protected by the flexible carrier strip 312.

The belt 314 may for example be made of polymer material, for example of elastomeric polymeric material. Being flexible, the belt 314 may be easily folded around a multitude of principal folding axis F along the width direction, perpendicularly to the strip elongation path and to the thickness of the belt 314. Being flexible, the belt 314 may also be twisted around a longitudinal axis parallel to the strip elongation path, but such twisting is not a compulsory feature of the foldable strip 310. Being flexible, the belt 314 may exhibit some amount of flexing around a thickness axis parallel to the thickness direction of the belt 314. However, such flexion is not a compulsory feature of the foldable strip 310, and it can be, in some cases, an undesirable feature, in which case it is easily limited for example by increasing the width of the belt the 314. Preferably, a flexible tie 314 comprises at least one unitary piece of material extending along the strip elongation path, as the belt 314 shown in FIGS. 4 and 5.

In the example embodiment of FIGS. 4 and 5, the unit medical vessels 111 of the plurality of unit medical vessels 111 are affixed on the flexible tie 314 at spaced intervals along the strip elongation path 311, preferably equally spaced intervals, by being removably inserted in semi-open receptacles 316. Each receptacle 316 may be either unitary with the belt 314, as illustrated, or may be in the form of an add-on component affixed to the belt.

The receptacles have a shape corresponding to at least a portion of the unit medical vessels 111, so that a unit medical vessel 111 can be snap-fitted into one receptacle and can be subsequently removed from said receptacle. In the shown example, where the unit medical vessel 111 is a barrel 102 of a syringe, each receptacle 316 is therefore in the shape of a partial cylinder having a C-shaped cross-section in a plane perpendicular to the width direction of the belt 314, thus perpendicular to the longitudinal vessel axis A of the unit medical vessel 111 that is to be inserted in the receptacle 316. The receptacle 316 is configured to exhibit sufficient flexibility to allow the C-shaped cross-section to be snap-fitted on a cylindrical portion of the unit medical vessel 111, such as the cylindrical outer surface 108 of a syringe barrel 102. Snap-fit connection is particularly advantageous because it allows for easy introduction and extraction of the unit medical vessel 111, and also ensures reliable fixing of the unit medical vessel 111 on the flexible tie 314.

In the first variant shown on FIG. 6, the flexible tie 314 comprises two facing belts 314, 314', which extend parallel to each other along the strip elongation path. Each of the two facing belts 314, 314' have facing half-receptacles 318, 318' which, when the two facing belts 314, 314' are pressed face to face one against the other, form together a receptacle 316 for a unit medical vessel 111. The two facing belts of 314, 314' may be disjoined one from the other along a direction parallel to the thickness direction of the belts, allowing either introduction or extraction of a unit medical vessel 111 into or from a corresponding receptacle 316. In the example, the two facing belts 314, 314' comprise complementary snap projections 320 and detents 320' which releasably lock the two facing belts together face to face, while, when released, allowing the two belts to be disjoined to allow introduction or extraction of the unit medical vessels from the corresponding receptacles 316.

In both examples of FIG. 5 and FIG. 6, the flexible tie 314 is foldable at least around said plurality of principal folding axis F spaced apart along the strip elongation path 311. In these examples, the flexible belts are flexible around a principal folding axis, parallel to the width dimension of the belt, at least at any location between two receptacles 316 along the strip elongation path 311.

In some embodiments, the flexible tie is flexible along its entire length along the strip elongation path 311. However, in some variants of the embodiments shown in FIGS. 4, 5 and 6, the flexible tie 314 may comprise flexible portions and rigid portions. For example, in those examples, the portions of the flexible tie 314 which form of the receptacles 316 could be rigid, being interconnected by flexible portions. In such a case, the foldable carrier strip 312 comprises several successive rigid segments 316 which extends along a portion of the strip elongation path 311 and on which the unit medical vessels 111 of the plurality of unit medical vessels are affixed at spaced intervals along the strip elongation path 311, preferably equally spaced intervals, and wherein two successive rigid segments 316 along the strip elongation path 311 are articulated one to the other around one of said principal folding axis F, by the interconnecting flexible portions.

In the second variant of FIGS. 7 to 10, the foldable strip 310 of unit medical vessels comprises a series of connectors 322 where each connector 322 extends between two unit medical vessels 111, and where each of said two unit medical vessels 111 is removably affixed to the connector 322. In this variant the foldable strip 310 of unit medical vessels comprises the plurality of unit medical vessels 111, and the connectors 322 connecting the plurality of unit medical vessels 111

In the second variant of FIGS. 7 to 10, two successive connectors 322, having a common unit medical vessel 111 affixed respectively to the two successive connectors 322, are independent from one another and said unit medical vessel is independently and removably affixed to each of the two successive connectors. In this example the two successive connectors 322 are only indirectly connected one to the other, via the common unit medical vessel 111 on which both of said successive connectors 322 are affixed. Preferably, each connector 322 is affixed to a unit medical vessel 111 by a snap fit connection. Preferably, each connector 222 has a first snap fit connection 324 for fixing the connector 322 to a first unit medical vessel 111, and a second snap fit connection 326 for fixing the same connector 322 to the second unit medical vessel 111, successive to the first unit medical vessel 111 along the strip elongation path 311. The first snap fit connection 324 and the second snap fit connection 326 of a given connector 322 are spaced apart along the strip elongation path 311. For a given unit medical vessel 111, the first snap fit connection 324 of the first connector 322 and the second snap fit connection 326 of a second connector 322 are snap fit on said given unit medical vessel 111.

In the second variant of FIGS. 7 to 10, all the connectors 322 are identical. In order to make sure that the first snap fit connection 324 of the first connector 322 and the second snap fit connection 326 of a second connector 322, which are snap fit on a given unit medical vessel 111, do not interfere one with the other, the first snap fit connection 324 and the second snap fit connection 326 are offset one compared the other along the direction of the longitudinal vessel axis A. In the shown example, the second snap fit connection 326 is formed of two portions 326a, 326b, which are offset one to the other along the direction of the longitudinal vessel axis A, to form a fork. The two portions 326a, 326b of the second snap fit connection 326 are offset by a distance sufficient for receiving, without interference, the first snap fit connection 324 of another connector 322 between the two portions 326a, 326b.

In other non-illustrated examples, successive connectors could be of different shapes to avoid interference at their respective connections on a given unit medical vessel 111.

In the second variant of FIGS. 7 to 10, the snap fit connection of each connector on a unit medical vessel 111 allows for the rotation of the connector with the respect to the unit medical vessel 111 around the longitudinal vessel axis A. Therefore, in such a foldable strip 310, the unit medical vessels 111 form an articulation rod between the two successive connectors 322. In such a case, the connector 322 may be rigid. In such a case, each of the principal folding axis F corresponds to the longitudinal vessel axis A of one of the unit medical vessels 111.

In a variant, the connector 322 may comprise a central portion, linking the first snap fit connection 324 and the second snap fit connection 326, which is flexible, in particularly flexible around at least one principal folding axis perpendicular to the strip elongation path 311. In such a case, the snap fit connection of each connector on a unit medical vessel 111 does not necessarily allow for the rotation of the connector with the respect to the unit medical vessel 111 around the longitudinal vessel axis A.

Each connector 322 is for example made of plastic material.

In the example of FIGS. 7 to 10, the snap fit connection of each connector has a C-shaped cross-section when viewed along an axis perpendicular to the longitudinal vessel axis A of the unit medical vessel 111 on which the connector is to be mounted. The C-shape cross-section is configured to showing sufficient flexibility to allow the C-shaped cross-section to be snap-fitted on a cylindrical portion of the unit medical vessel 11, such as the cylindrical outer surface 108 of a syringe barrel 102.

In the example of FIGS. 7 to 10, each unit medical vessel 111 is individually removably affixed to two successive connectors 322 by a snap-fit connection allowing each unit medical vessels 111 to be removably and rotatably affixed to the two connector 322. However, in some embodiments, at least one of said two unit medical vessels 111 may be removably affixed to at least one connector 322 through a removable adhesive connection that preferably leaves no adhesive on the vessel after removal. Each unit medical vessel can be removed from at least one connector, preferably from each connector, when needed, at the appropriate processing station, such that each unit medical vessels may be processed individually. Preferably, each unit medical vessel can be removed from a given connector 322 by the mere application of opposite separation forces respectively on the unit medical vessel and on the connector 322. In other words, the separation of a unit medical vessel from the connector 322 preferably does not require any other action that holding the unit medical vessel and the connector 322 and displacing them away one from the other. Preferably, each unit medical vessel can be removed from the connector 322 without any damage to unit medical vessel. Preferably, each unit medical vessel can be removed from the connector 322 without any damage to the connector 322, so that the connector 322 may be subsequently reused for forming a new foldable strip 310. However, in some embodiments, the removal of a unit medical vessel 111 from a connector 322 may involve partial or complete destruction of the connector 322, which is then disposable, but preferably made of recyclable material.

In the variant of FIGS. 7-10, the width W of each connector 322 is less than the height of the unit medical vessels 111 along the same direction. In other words, the unit medical vessels 111 exceed the limits of the connectors 322 along the width direction, at least on one side, or, as in the shown variant, on both sides along the width direction of the flexible strip 310. In an alternate design, the shape each connector 322 may be such that each unit medical vessel 111 is contained within the limits of the series of connectors 322 along the width direction of the flexible strip 310.

Figure 11:
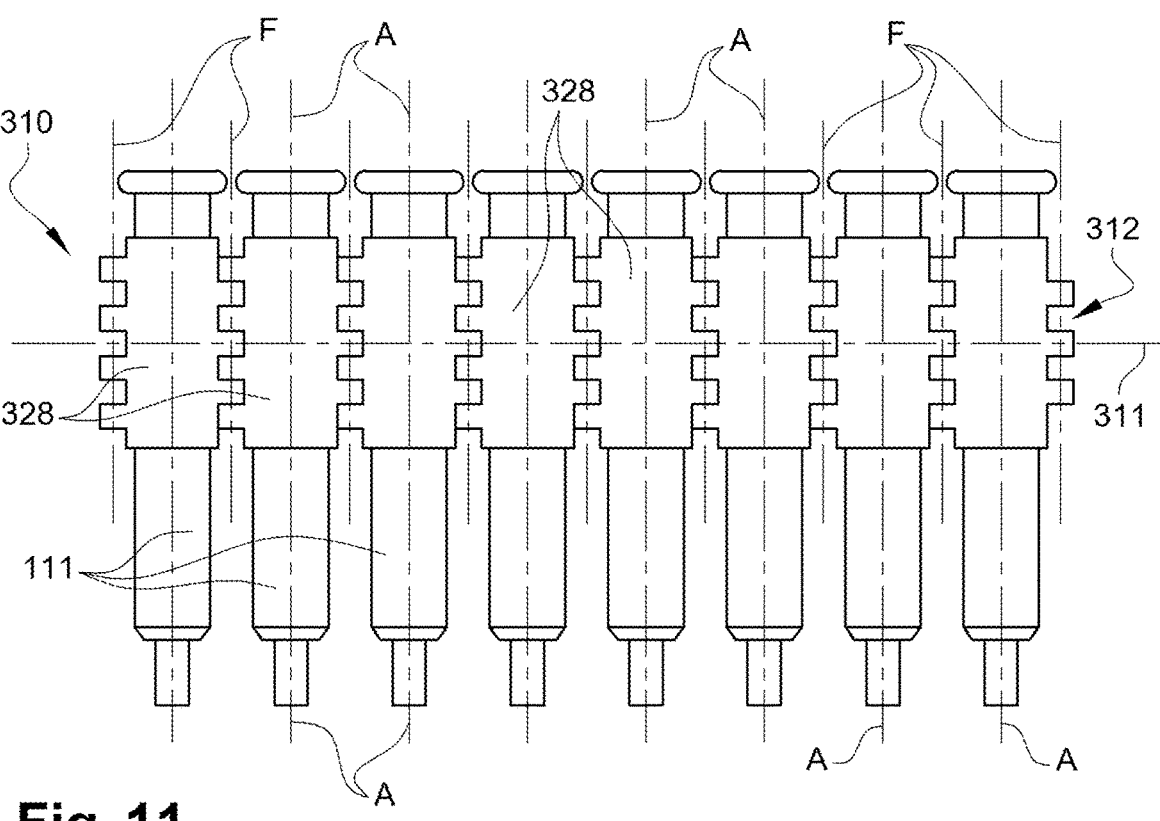
FIG. 11.
Figure 12:
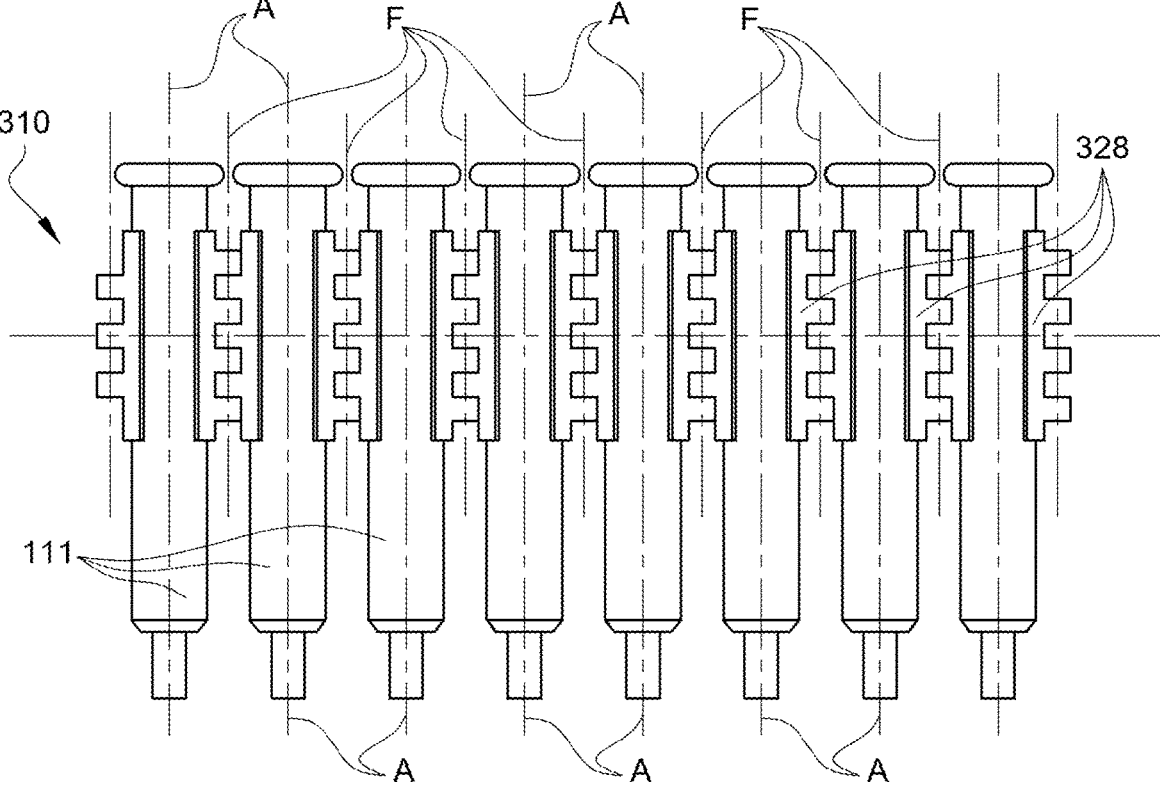
FIG. 12.

In the third variant of FIGS. 11 and 12, the foldable strip 310 has a foldable carrier strip 312 that comprises several successive rigid segments 328. Each rigid segment of 328 extends along a portion of the strip elongation path 311. Two successive rigid segments 328 are articulated one to the other around a principal folding axis F, independently of the unit medical vessels 111. A given rigid segment 328 is thus articulated, at each of its two extremities along the strip elongation path 311, respectively to a first and to a second neighboring rigid segment 328, respectively around a first and second principal folding axis F.

In the shown example, each rigid segment 328 carries unit medical vessel 111. However, it could be provided that only one every two rigid segments, or one every three rigid segments, etc. . . . , carries a unit medical vessel 111. Preferably, a unit medical vessel 111 is affixed to a rigid segment 328 by a snap fit connection and/or through a removable adhesive connection that preferably leaves no adhesive on the vessel after removal, as described above in relation to the first embodiment. A snap-fit connection may be achieved by a C-shaped cross-section when viewed along an axis perpendicular to the longitudinal vessel axis A of the unit medical vessel 111 that is to be affixed to the rigid segment. The C-shape cross-section is configured to showing sufficient flexibility to allow the C-shaped cross-section to be snap-fitted on a cylindrical portion of the unit medical vessel 11, such as the cylindrical outer surface 108 of a syringe barrel 102.

In the shown example, all rigid segments 328 are identical. However, two successive rigid segments 328 may be different. For example, a rigid segment 328 carrying unit medical vessel 111 may be different from a rigid segment 328 not carrying any unit medical vessel. In this variant, the foldable strip 310 of unit medical vessels comprises the foldable carrier strip 312 of successive rigid segments 328 and comprises the unit medical vessels 111, which are affixed on the foldable carrier strip 312.

The primary container 301 may take various forms. The primary container 301 accommodates at least one foldable strip 310 of unit medical vessels 311.

In some embodiments, as those illustrated in the figures, the primary container contains, in its closed state, a single foldable strip 310 of unit medical vessels 111. However, the packaging 300 may be configured in such a way that the primary container 301 contains, in its closed state, several foldable strips 310 of unit medical vessels 111.

Figure 15:
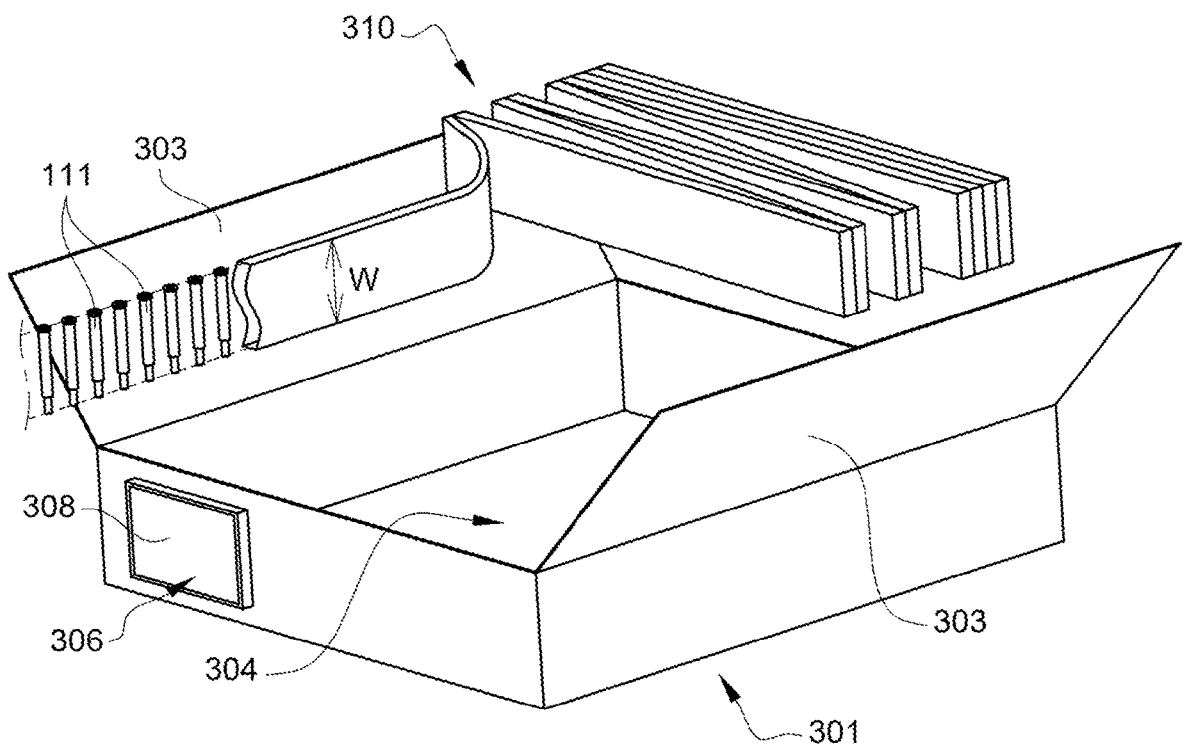
FIG. 15.
Figure 16:
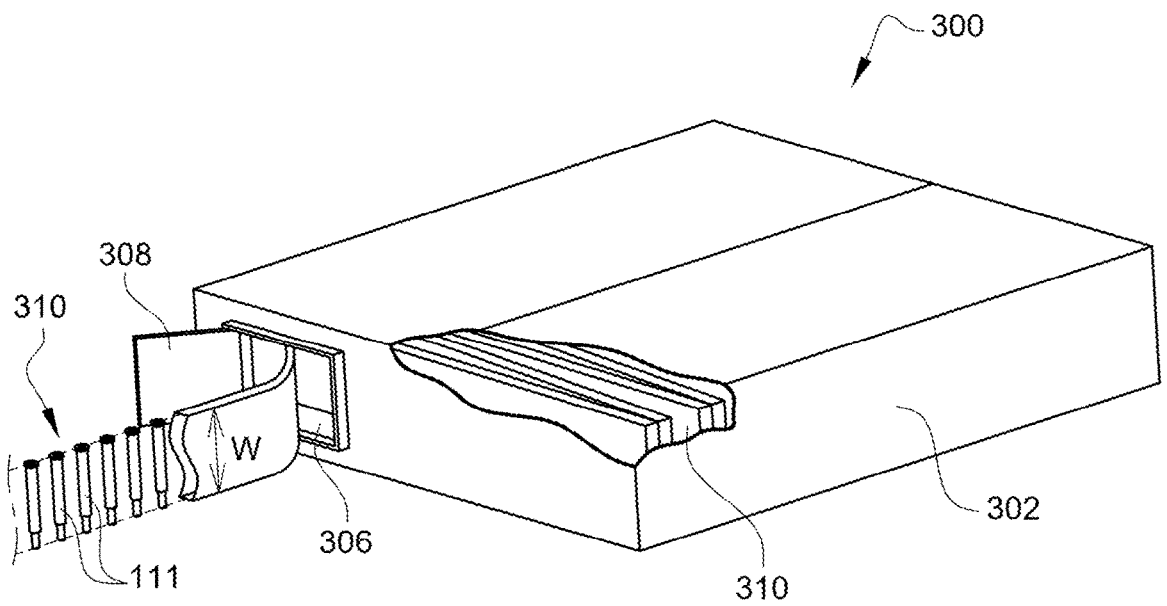
FIG. 16.

In the packaging 300, when the foldable strip 310 of unit medical vessels is contained in the primary container 301 in its closed state, the foldable strip 310 is in a folded state. In its folded state, the foldable strip 310 is compact so that the size of the primary container can be reduced. In the example of FIGS. 13 and 14, the foldable strip 310 is, in its folded stated, folded for example in a spiral, so that the strip elongation path 311 follows a spiral. In the example of FIGS. 15 and 16, the foldable strip 310 is folded in an accordion fold, so that the strip elongation pass 311 follows a zigzag line. Other forms of folding are possible. In all cases, the folding of the foldable strip 310 of unit medical vessels occurs around a plurality of principal folding axis spaced apart along the strip elongation path 311, all parallel to a principal folding axis direction perpendicular to the strip elongation path. Therefore, the strip elongation path 311 is folded in a plane, said plane containing the folded strip elongation path 311. In the case of elongated unit medical vessels 111 having a longitudinal axis A, the longitudinal vessel axis A of each unit medical vessel 111 of the foldable strip 310 is perpendicular to the plane containing the folded strip elongation path 311.

In some embodiments, such as shown in FIGS. 13 and 14, the peripheral wall 302 of the primary container 301 has at least one flexible wall portion. In the example of FIGS. 13 and 14, the peripheral wall 302 of the primary container 301 is made of flexible material and forms a bag. For example, the peripheral wall 301 of the primary container may be made with conventional foil material used for making foil packaging in the pharmaceutical industry.

In some embodiments, the peripheral wall 302 of the primary container 301 has at least one rigid wall portion. In the example of FIGS. 15 and 16, the peripheral wall 302 of the primary container 301 is made of rigid material and forms a box. The rigid material may be a sheet of plastic material, such as polyethylene or polypropylene. The rigid material may for example be a sheet of corrugated plastic comprising two outside substantially flat plastic sheets separated by small plastic beams running parallel to them and joining the two outside plastic sheets.

The external shape of the primary container in 301 is for example that of a parallelepiped. Having primary containers of parallelepiped shape has the advantage that the primary containers 301 can be easily stacked for transport, as shown for example in FIG. 17 where it is shown that the primary containers 301 can be stacked and palletized for transport.

In all cases, when it is in its closed state, the primary container 301 is hermetically sealed so that the foldable strip 310 of unit medical vessels 111 cannot be fouled or contaminated, in the sense that no particle or germ coming from the exterior of the primary container 301 can reach the units medical vessels 111 of the foldable strip 310.

In some examples, in the closed state of the primary container 301, the inner volume 304 of the primary container 301 may be filled with a fluid, for example a gas, such a fluid in the inner volume 304 being under a pressure superior to the atmospheric pressure, for example at least 50 millibars above atmospheric pressure, preferably at least 100 millibars above atmospheric pressure.

The presence of pressurized fluid inside the inner volume 304 tends to rigidify the peripheral wall 302 of the primary container 301. This provides increased strength to the packaging 300, and thus increased protection of the unit medical vessels 111 against external mechanical shocks. Use of such a pressurized inner fluid is particularly advantageous when the peripheral wall 302 of the primary container 301 comprises at least one flexible wall portion or, as in the example of FIGS. 13 and 14, is substantially entirely made of flexible material.

The presence of pressurized fluid inside the inner volume 304 has also the advantage of providing an indication of whether the integrity of the primary container may have been compromised. Indeed, as long as it can be perceived that the inner volume is still pressurized, especially when the peripheral wall of the primary container has at least one flexible wall portion, then it can be deduced that no fouling of the unit vessel containers 111 can have occurred after the closure of the primary container 301. The packaging 300 is then a tamper evident packaging.

In some examples, in the closed state of the primary container 301, the inner volume 304 of the primary container 301 may be filled with a sterilizing fluid, for example a gas containing a sterilizing agent. An example of such a sterilizing agent is ethylene oxide (ETO). In some embodiments, such a sterilizing fluid may be under a pressure superior to the atmospheric pressure. The presence of the sterilizing fluid may be permanent from the closing of the primary container 301 to its opening, or it can be temporary, for example only during a sterilizing step of the fabricating process. For example the sterilizing fluid may be introduced in the primary container when or after the closing of the container with the foldable strip 310 of unit medical vessels at 111 inside, maintained during a sterilizing step, and then remove totally or at least partially, and possibly replaced totally or partially by a neutral fluid such as air or such as nitrogen. Fluid introduction and removal, in the inner volume of the primary container, may be performed for example through a dedicated fluid introduction port as described hereunder.

The transfer port 306 of the primary container three or one is preferably arranged on the peripheral wall 302. Preferably, the transfer port 306 comprises a peripheral frame 307 which surrounds an opening, said opening being closed by the closure 308 in the closed configuration. The peripheral frame 307 and the corresponding opening are shaped and sized to allow the transfer or extraction of the foldable strip 310 of unit medical vessels 111 through the transfer port 306. The extraction of the foldable strip 310 of unit medical vessels 111 is performed by unfolding progressively the foldable strip 310, so that the strip elongation path 311 is substantially perpendicular to the opening defined by the transfer port 306. During this extraction, the unit medical vessel 111 contained in the foldable strip 310 are thus transferred out one by one through the opening of the transfer port 306 as the foldable strip is progressively transferred out through that opening.

In some embodiments, the closure 308 of the transfer port 306 may be a mere film closure, such as an opercula, which may be ripped off for opening the transfer port 306. In the example of FIGS. 15 and 16, the closure 308 of the transfer port 306 is a hatch door which can be pivoted between a closed configuration shown in FIG. 15 and an open configuration shown in FIG. 16.

However, in a preferred embodiment, the transfer port 306 is preferably configured as a part of a so-called Rapid Transfer Port (RTP) commonly used in the pharmaceutical industry. More precisely, the transfer port 306 of the primary container 301 and the input docking port 226 of the closed enclosure 224 of the filling station 220 are complimentary one to the other, so as to form such a so-called Rapid Transfer Port (RTP). In such a case, the input docking port 226 of the closed enclosure 224 of the filling station 220 is commonly designated as being the "alpha port" of the Rapid Transfer Port (RTP), and the transfer port 306 of the primary container 301 is commonly designated as being the "beta port" of the Rapid Transfer Port (RTP). Thereby, the input docking port 226 of the closed enclosure 224 of the filling station 220 is compatible with the transfer port 306 of the primary container 301 of the packaging 301 to achieve a sealed docking of the primary container 301 on the processing station 220.

Figures 17, 18:
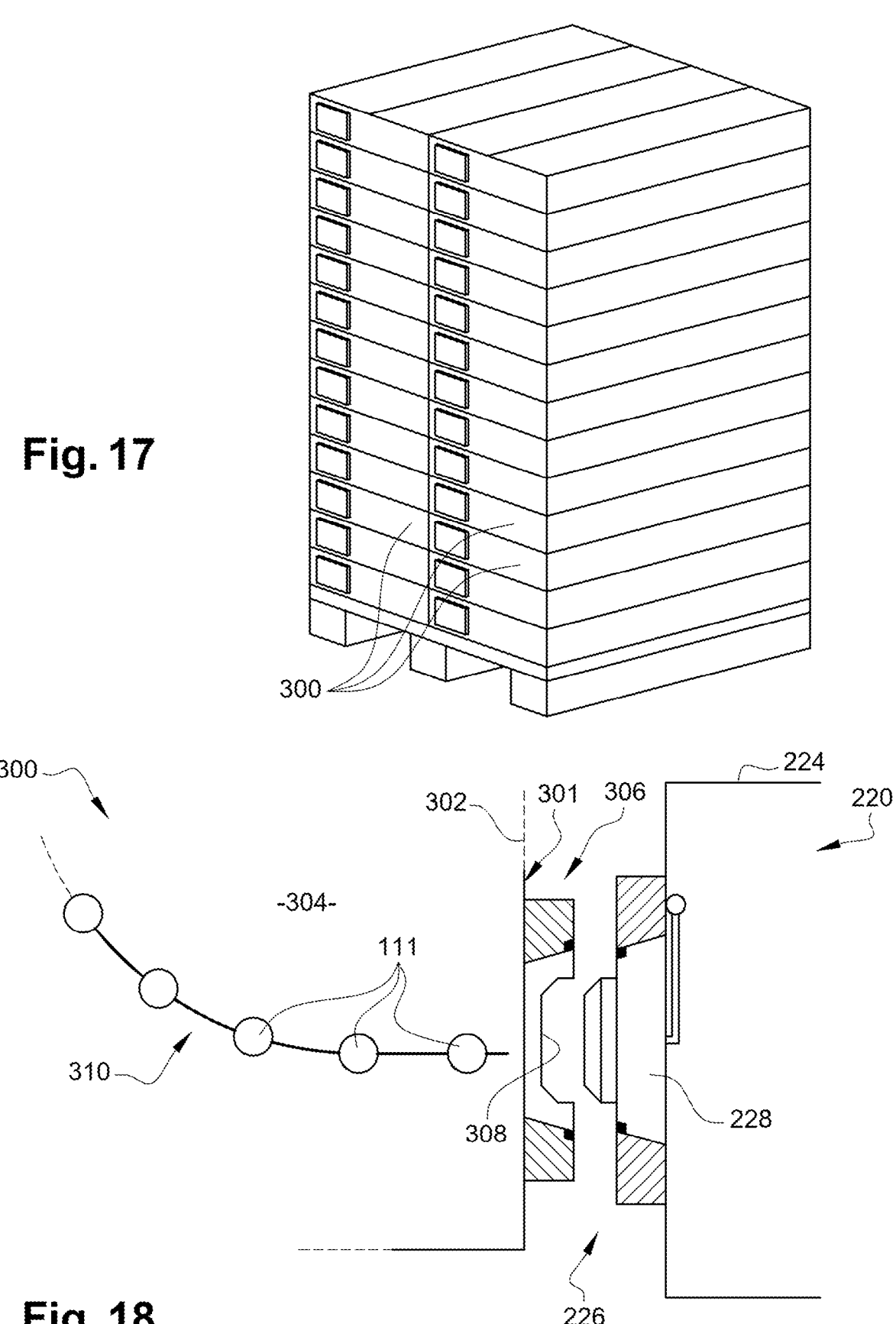
FIG. 17.
FIG. 18.
Figure 19:
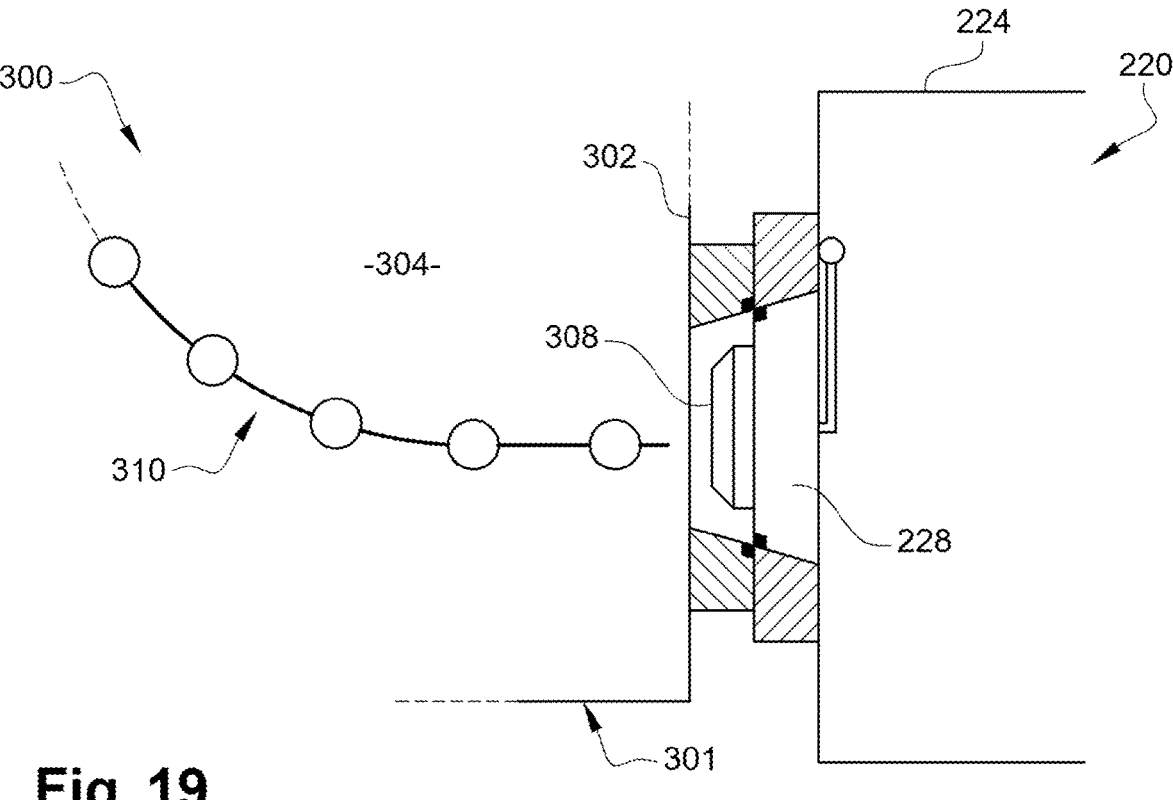
FIG. 19.
Figure 20:
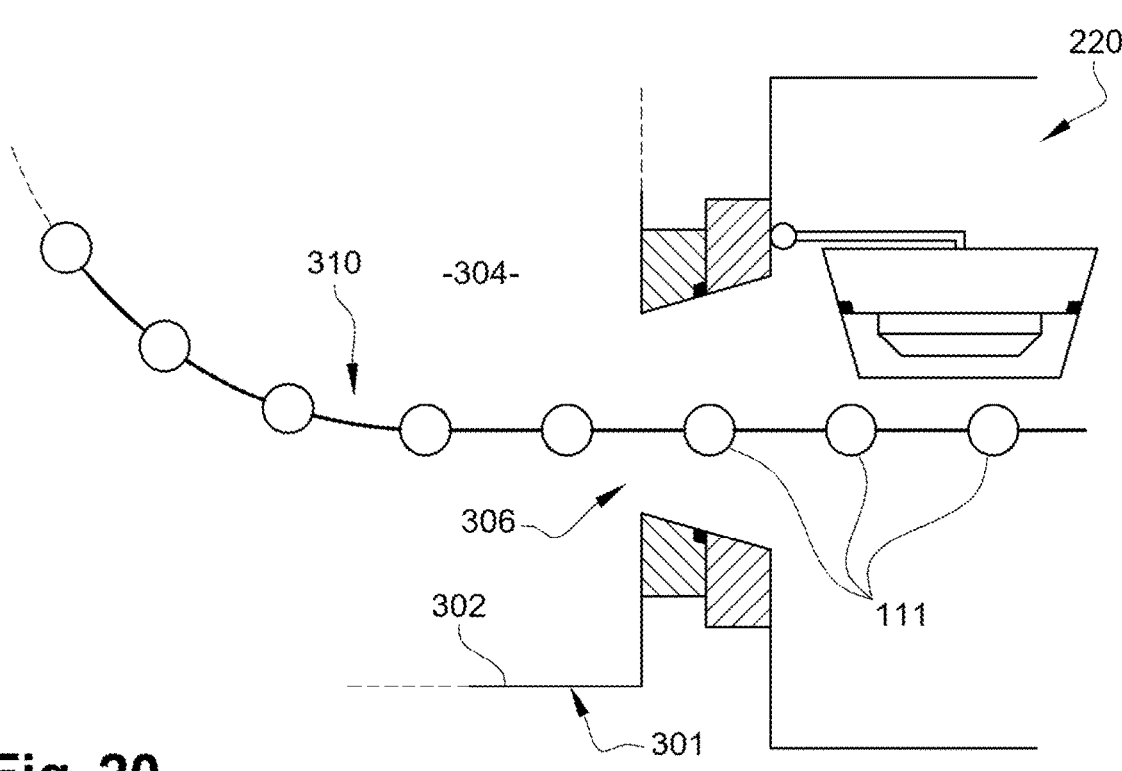
FIG. 20.

A conventional design and operation of a Rapid Transfer Port (RTP) is schematically illustrated in FIGS. 18, 19 and 20. The input docking port 226 of the closed enclosure 224 of the second processing station 220 comprises a door 228 which can be switched between a closed configuration, shown in FIGS. 18 and 19, and an open configuration as shown on FIG. 20. The door 228 has an internal side turned towards the inside of the closed enclosure 224, and an external side turned towards the outside of the closed enclosure 224. In the shown example, the door 228 opens towards the inside of the closed enclosure 224. Before the docking of the transfer port 306 onto the input docking port 226, as shown in FIG. 18, the closure 308 of the transfer port 306 maintains the inner volume 304 of the primary container 301 in the closed state and the door 228 maintains the closed enclosure closed. When the transfer port 306 is docked onto the input docking port 226, as shown in FIG. 19, the closure 308 contacts the door 228 and both become interconnected.

Once this interconnection is achieved, the door 228 of the input docking port 226 may be switched to its open configuration, and carries with it the closure 308, thereby opening the transfer port 306 of the primary container 301, as shown in FIG. 20. This therefore opens at the communication between the inner volume 304 of the primary container 301 with the inside of the closed enclosure 224 of the second processing station 220. At that moment, as shown in FIG. 20, the foldable strip 310 of unit medical vessels 111 may be progressively transferred out the primary container 301, through the rapid transfer port, by progressively unfolding the foldable strip 310. Thus, the unit medical vessels 111 of the foldable strip 310 are transferred from the primary container 301 to the inside of the closed enclosure 224 of the processing station 220 without contact with the external environment.

In some embodiments, it may be provided that the strip 310 is attached to the closure 308 or to the transfer port 306 in order to facilitate the process of transferring the strip 310 out of the primary container through the transfer port 306, by making the strip immediately accessible upon the opening of the closure 308, facilitating the initiating/priming of the extraction of the strip.

In some embodiments, the primary container 301 may have a main opening which is distinct from the transfer port 306. In such a case, the foldable strip 310 of unit medical vessels 111 is introduced in the inner volume 304 of the primary container 301 through the main opening. The main opening is hermetically sealed when the primary container 301 is in its closed state. For example in the embodiment of FIGS. 15 and 16, the box shape primary container 301 comprises, on one side, two flaps 303 which can pivot to open the side of the box to allow for the insertion of the foldable strip 310 into the inner volume 304 of the primary container 301. The flaps 303 are folded back in place and hermetically sealed after the foldable strip 310 has been inserted in the inner volume 304. In the example embodiment of FIGS. 13 and 14, the flexible bag primary container 301 has one extremity 305 which forms an opening and which can be sealed and rolled after the foldable strip 310 has been inserted in the inner volume 304. Because the extremity 305 of the flexible bag primary container 301 is rolled, the exact size of the primary container 301 can be adapted to the dimensions of the folded foldable strip 310 of unit medical vessels 111.

In those cases where the inner volume 304 of the primary container 301 is filled with a fluid, the primary container 31 may have a fluid introduction port 307 which is distinct from the transfer port 306. Alternatively, the introduction of the foldable strip 310 of unit medical vessels may be performed in an enclosure filled with sterilizing fluid.

The different features of the embodiments described above can be used in combination and used with other embodiments as long as the combined parts are not inconsistent with or interfere with the operation of the device and assembly. This invention is not limited in its application to the details of construction and the arrangement of components set forth in the following description or illustrated in the drawings. The embodiments herein are capable of being modified, practiced or carried out in various ways. The phraseology and terminology used herein is for the purpose of description and should not be regarded as limiting. The use of "including," "comprising," or "having" and variations thereof herein is to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not limited to physical or mechanical connections or couplings. Further, terms such as up, down, bottom, and top are relative, and are to aid illustration, but are not limiting. The embodiments are not intended to be mutually exclusive so that the features of one embodiment can be combined with other embodiments as long as they do not contradict each other. Terms of degree, such as "substantially", "about" and "approximately" are understood by those skilled in the art to refer to reasonable ranges around and including the given value and ranges outside the given value, for example, general tolerances associated with manufacturing, assembly, and use of the embodiments. The term "substantially" when referring to a structure or characteristic includes the characteristic that is mostly or entirely present in the structure.

The terminology used herein is for the purpose of describing particular aspects only and is not intended to be limiting of the disclosure. As used herein, the singular forms "a," "an," and "the" are intended to include the plural forms as well, unless the context clearly indicates otherwise. As used herein, the term "and/or" includes any and all combinations of one or more of the associated listed items. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

It will be understood that, although the terms first, second, etc., may be used herein to describe various elements, these elements should not be limited by these terms. These terms are only used to distinguish one element from another. For example, a first element could be termed a second element, and, similarly, a second element could be termed a first element without departing from the scope of the present disclosure.

Unless otherwise defined, all terms (including technical and scientific terms) used herein have the same meaning as commonly understood by one of ordinary skill in the art to which this disclosure belongs. It will be further understood that terms used herein should be interpreted as having a meaning consistent with their meaning in the context of this specification and the relevant art and will not be interpreted in an idealized or overly formal sense unless expressly so defined herein.

It is to be understood that the present disclosure is not limited to the aspects described above and illustrated in the drawings; rather, the skilled person will recognize that changes and modifications may be made within the scope of the appended claims.

The invention claimed is:

1. A packaging for a plurality of unit medical vessels, comprising:

at least one foldable strip of unit medical vessels in which a plurality of unit medical vessels are connected one to the other at spaced intervals along a strip elongation path, wherein the foldable strip is foldable at least around a plurality of principal folding axis (F) spaced apart along the strip elongation path, each principal folding axis (F) being parallel to a principal folding axis direction perpendicular to the strip elongation path; and a primary container having a peripheral wall and having a closed state in which the primary container defines a hermetically sealed inner volume inside the peripheral wall, wherein the foldable strip of unit medical vessels is received in said inner volume of the primary container, and wherein the primary container has a transfer port having a closure, the closure having a closed configuration where, in the closed state of the primary container, it hermetically closes the transfer port, and an open configuration where it allows the at least one foldable strip of unit medical vessels to be transferred out of the primary container through the transfer port.

2. The packaging according to claim 1, wherein the primary container contains, a single foldable strip of unit medical vessels.

3. The packaging according to claim 1, wherein, in the closed state of the primary container, the inner volume of the primary container is filled with a sterilizing fluid.

4. The packaging according to claim 1, wherein, in the closed state of the primary container, the inner volume of the primary container is filled with a fluid under a pressure superior to the atmospheric pressure.

5. The packaging according to claim 1, wherein the peripheral wall of the primary container has at least one flexible wall portion.

6. The packaging according to claim 1, wherein the peripheral wall of the primary container is flexible.

7. The packaging according to claim 1, wherein the peripheral wall of the primary container has at least one rigid wall portion.

8. The packaging according to claim 1, wherein the peripheral wall of the primary container is rigid.

9. The packaging according to claim 1, wherein the primary container has a main opening which is distinct from the transfer port, through which the at least one foldable strip of unit medical containers is introduced in the inner volume of the primary container, and which is hermetically sealed when the primary container is in its closed state.

10. The packaging according to claim 1, wherein the primary container has a sterilizing fluid introduction port which is distinct from the transfer port.

11. The packaging according to claim 1, wherein the unit medical vessels of the plurality of unit medical vessels are arranged in a single row along the strip elongation path of the foldable strip of unit medical vessels.

12. The packaging according to claim 1, wherein the unit medical vessels of the plurality of unit medical vessels are each elongated along a vessel axis (A) parallel to the principal folding axis direction.

13. The packaging according to claim 1, wherein the foldable strip of unit medical vessels comprises a foldable carrier strip on which the unit medical vessels of the plurality of unit medical vessels are affixed along the strip elongation path, wherein the foldable carrier strip is foldable at least around said plurality of principal folding axis spaced apart along the strip elongation path.

14. The packaging according to claim 13, wherein the unit medical vessels are each individually removably affixed on the foldable carrier strip.

15. The packaging according to claim 13, wherein the foldable carrier strip comprises a flexible tie which extends along the strip elongation path and on which the unit medical vessels or the plurality of unit medical vessels are affixed along the strip elongation path, wherein the flexible tie is foldable at least around said plurality of principal folding axis spaced apart along the strip elongation path.

16. The packaging according to claim 13, wherein the foldable carrier strip comprises several successive rigid segments which each extend along a portion of the strip elongation path and on which the unit medical vessels of the plurality of unit medical vessels are affixed at equally spaced intervals along the strip elongation path, and wherein two successive rigid segments along the strip elongation path, are articulated one to the other around one of said principal folding axis (F).

17. The packaging according to claim 1, wherein the foldable strip of unit medical vessels comprises a series of connectors where each connector extends between two unit medical vessels, and wherein each of said two unit medical vessels is removably affixed to the connector.

18. The packaging according to claim 17, wherein two successive connectors, having a common unit medical vessel affixed respectively to the two successive connectors, are independent from one another and said unit medical vessel is independently and removably affixed to each of to the two successive connectors.

19. A processing system for processing unit medical vessels, wherein the processing system comprises a processing station having a closed enclosure which is sealed from an external environment outside of the enclosure, wherein the unit medical vessels are processed inside the closed enclosure, wherein the enclosure of the processing station has an input docking port, wherein the input docking port is compatible with the transfer port of a primary container of a packaging according to claim 1 to achieve a sealed docking of the primary container on the processing station, and wherein, when the primary container is sealingly docked on the processing station, the closure of the transfer port may be set to its open configuration where the transfer port allows communication between the inner volume of the primary container and the inside of the closed enclosure of the processing station, and where the transfer port allows the foldable strip of unit medical vessels to be transferred out of the primary container through the transfer port and the input docking port into the inside of the closed enclosure of the processing station, without contact with the external environment.

20. The processing system according to claim 19, wherein the processing system is a filling system for filing the unit medical vessels with a medical product, wherein the processing station is a filling station having a closed enclosure which is sealed from an external environment outside of the closed enclosure and in which the unit medical vessels are filled with a medical product inside the closed enclosure.

\* \* \* \* \*